(12) United States Patent
Mehta et al.

(10) Patent No.: US 7,521,573 B2
(45) Date of Patent: Apr. 21, 2009

(54) IONIC ORGANOSILICON COMPOUNDS AND COMPOSITIONS THEREOF

(75) Inventors: Praksh Vithaldas Mehta, Gujarat (IN); Ajay Ishwarlal Ranka, Guarat (IN)

(73) Assignee: Zydex Industries, Gujarat (IN)

( * ) Notice: Subject to any disclaimer, the term of this patent is extended or adjusted under 35 U.S.C. 154(b) by 0 days.

(21) Appl. No.: 11/468,100

(22) Filed: Aug. 29, 2006

(65) Prior Publication Data

US 2008/0009643 A1    Jan. 10, 2008

(30) Foreign Application Priority Data

Jul. 7, 2006    (IN) ............... 1070/MUM/2006

(51) Int. Cl.
   *C07F 7/04*    (2006.01)
(52) U.S. Cl. ..................................... 556/413
(58) Field of Classification Search .......... 556/423, 556/400, 482, 413
   See application file for complete search history.

(56) References Cited

U.S. PATENT DOCUMENTS

| | | | |
|---|---|---|---|
| 2,115,622 A | 4/1938 | Dawson | |
| 2,721,812 A | 10/1955 | Iler | |
| 3,352,894 A | 11/1967 | Crain et al. | |
| 3,560,385 A | 2/1971 | Roth | |
| 3,730,701 A | 5/1973 | Isquith et al. | |
| 3,772,062 A | 11/1973 | Shur et al. | |
| 3,794,736 A | 2/1974 | Abbott et al. | |
| 3,814,739 A | 6/1974 | Takeda | |
| 3,849,357 A | 11/1974 | Wolf | |
| 3,860,709 A | 1/1975 | Abbott et al. | |
| 3,879,206 A | 4/1975 | Nestler et al. | |
| 3,914,476 A | 10/1975 | Nitzsche et al. | |
| 3,955,985 A | 5/1976 | Bosch et al. | |
| 4,002,800 A | 1/1977 | Nestler et al. | |
| 4,005,028 A * | 1/1977 | Heckert et al. ............... | 510/180 |
| 4,005,030 A * | 1/1977 | Heckert et al. ............... | 510/180 |
| 4,209,432 A | 6/1980 | Roth | |
| 4,273,813 A | 6/1981 | Meddaugh | |
| 4,282,366 A | 8/1981 | Eudy | |
| 4,342,796 A | 8/1982 | Brown | |
| 4,390,712 A * | 6/1983 | Karl et al. ................... | 556/413 |
| 4,408,996 A | 10/1983 | Baldwin | |
| 4,414,268 A | 11/1983 | Baldwin | |
| 4,417,066 A | 11/1983 | Westall | |
| 4,478,911 A | 10/1984 | Price | |
| 4,486,476 A | 12/1984 | Fritsch | |
| 4,504,541 A | 3/1985 | Yasuda | |
| 4,601,902 A * | 7/1986 | Fridd et al. ............ | 424/70.122 |
| 4,615,937 A | 10/1986 | Bouchette | |
| 4,631,207 A | 12/1986 | Price | |
| 4,648,904 A | 3/1987 | De Pasquale | |
| 4,692,374 A | 9/1987 | Bouchette | |
| 4,717,599 A | 1/1988 | Merrill | |
| 4,741,773 A | 5/1988 | Kuroda | |
| 4,753,977 A | 6/1988 | Merrill | |
| 4,786,531 A | 11/1988 | Hodson | |
| 4,845,256 A | 7/1989 | Mebes | |
| 4,846,886 A | 7/1989 | Fey | |
| 4,847,088 A | 7/1989 | Blank | |
| 4,865,844 A | 9/1989 | Blank et al. | |
| 4,874,431 A | 10/1989 | Fey | |
| 4,877,654 A | 10/1989 | Wilson | |
| 4,899,747 A | 2/1990 | Garren | |
| 4,908,355 A | 3/1990 | Gettings et al. | |
| 4,921,701 A | 5/1990 | Blehm Blank | |
| 4,985,023 A | 1/1991 | Blank et al. | |
| 4,990,338 A | 2/1991 | Blank et al. | |
| 5,013,459 A | 5/1991 | Gettings et al. | |
| 5,019,173 A | 5/1991 | Gettings et al. | |
| 5,051,129 A | 9/1991 | Cuthbert et al. | |
| 5,073,195 A | 12/1991 | Cuthbert et al. | |
| 5,110,684 A | 5/1992 | Cooper | |
| 5,169,625 A | 12/1992 | Blank | |
| 5,209,775 A | 5/1993 | Bank et al. | |
| 5,300,327 A | 4/1994 | Stark-Kasley et al. | |
| 5,411,585 A | 5/1995 | Avery et al. | |
| 5,421,866 A | 6/1995 | Stark-Kasley et al. | |

(Continued)

FOREIGN PATENT DOCUMENTS

CA    2115622    9/1994

(Continued)

OTHER PUBLICATIONS

The International Search Report for PCT Application No. PCT/IN2006/00304; Filed Aug. 22, 2006; Date of Completion Oct. 5, 2008; Date of Mailing Oct. 23, 2008.

(Continued)

*Primary Examiner*—Daniel M Sullivan
*Assistant Examiner*—Chukwuma O Nwaonicha
(74) *Attorney, Agent, or Firm*—Alston & Bird LLP

(57) ABSTRACT

Ionic organosilicon compounds are provided comprising ethylene glycol functionality and aqueous compositions comprising such ionic organosilicon compounds; wherein the aqueous compositions are suitable for imparting water repellency to a wide variety of surfaces. The compositions of the present invention are prepared by dissolving ionic organosilicon compounds in water. Surprisingly, it has been found that the water soluble ionic organosilicon compounds, which have an ionic group, a hydrophobic group and at least one alkoxy group on silicon, of the present invention provide treated surfaces with excellent hydrophobicity.

11 Claims, No Drawings

U.S. PATENT DOCUMENTS

| | | | |
|---|---|---|---|
| 5,695,551 A | 12/1997 | Buckingham et al. | |
| 5,798,144 A | 8/1998 | Varanasi et al. | |
| 6,376,696 B1 * | 4/2002 | Raab et al. | 556/423 |
| 6,482,969 B1 | 11/2002 | Helmrick et al. | |
| 6,994,890 B2 | 2/2006 | Ohlhausen et al. | |

FOREIGN PATENT DOCUMENTS

| | | |
|---|---|---|
| EP | 0355765 | 2/1990 |
| JP | 3159975 | 7/1991 |
| WO | WO 00/72850 * | 7/2000 |

OTHER PUBLICATIONS

The Written Opinion for PCT Application No. PCT/IN2006/00304; Filed Aug. 22, 2006; Date of Completiion Oct. 5, 2008; Date of Mailing Oct. 23, 2008.

* cited by examiner

IONIC ORGANOSILICON COMPOUNDS AND COMPOSITIONS THEREOF

BACKGROUND OF THE INVENTION

This invention relates to ionic organosilicon compounds comprising ethylene glycol functionality and aqueous compositions comprising such ionic organosilicon compounds; wherein the compositions are suitable for applying to inorganic surfaces to impart water repellency.

Water resistance is an important issue in many types of construction including masonry and concrete. Resistance to water is of great importance since moisture absorption and its movement in these types of materials cause or contributes to problems such as expansion, shrinkage, cracking, staining, mildew, lowered resistance to freezing and thawing, chemical attack, corrosion of reinforcing steel, and damage to structures from settling. Due to these problems, various techniques have been used to render these types of surfaces water resistant including surface treatment of structures with water repellents. Water repellents that have been used in the past include oils, waxes, soaps, and resins. These repellants have been applied to surfaces by brush, roller, air spray, or airless spray techniques. One type of water repellent that has been used is organosilicon compounds. These compounds in organic solvents have been found to be useful for providing water resistance to brick, concrete, stucco, or terrazo surfaces.

As discussed in U.S. Pat. No. 5,073,195, the contents of which are hereby incorporated by reference, application of organosilicon compounds to surfaces for water proofing is well known in the art. The use of organosilicon compounds such as alkyltrialkoxy compounds for imparting water resistance has been known for at least 30 years. Traditionally, application of these compounds was carried out in flammable solvents such as ethanol, methanol and various liquid hydrocarbons. During application, volatile organic compounds (VOC) were heavily emitted. Due to these problems, significant efforts were employed to formulate a nonflammable composition for imparting water resistance to masonry and concrete surfaces. The first approach attempted included various water emulsions containing organosilicon compounds. However, these formulations failed to provide water resistance comparable to the solvent based compositions. In recognition of the shortcomings associated with the water emulsion formulation, formulations were developed to make alkyltrialkoxy silanes water soluble. Formulations of this type utilize water soluble amino and quaternary ammonium organosilanes along with alkyltrialkoxysilanes of the traditional formulations. The intent of these formulations was to exploit the soluble organosilanes to solubilize the alkyltrialkoxysilanes, which provided the water repellant characteristic.

In addition to water resistance, numerous types of construction materials benefit from treatment with an antimicrobial agent. Antimicrobial agents are chemical compositions that prevent microbial contamination and deterioration of materials. Possibly the most prevalent group of antimicrobials is quaternary ammonium compounds. The use of low level (1% or lower) quaternary ammonium silanes as antimicrobial agents is well known and taught in a wide variety of United States patents including U.S. Pat. Nos. 3,560,385; 3,794,736; and 3,814,739. Due to their antimicrobial qualities, their application is beneficial for a variety of surfaces, substrates, instruments and applications. Examples of such uses are described in U.S. Pat. Nos. 3,730,701; 3,794,736; 3,860,709; 4,282,366; 4,504,541; 4,615,937; 4,692,374; 4,408,996; and 4,414,268; the contents of which are hereby incorporated by reference. Application of an aqueous solution containing a quaternary ammonium silane is discussed in U.S. Pat. Nos. 4,921,701 and 5,169,625.

Relevant to the present invention are U.S. Pat. Nos. 5,209,775, 5,421,866, 5,695,551, CA 2,115,622 and JP 3,159,975. These patents are directed to water dispersible or water emulsion water repellent compositions of silicon compounds. The compositions disclosed in these patents contain (1) alkylalkoxy silane or siloxanes; (2) a water soluble silane; and (3) either aminosilane or quaternary ammonium silane. The role of soluble silane, aminosilane or ionic quaternary ammonium silane, in these compositions is to stabilize the alkylalkoxysilane, siloxane, or other water insoluble polymers in water.

The use of hydrophobic water insoluble silane based water repellents in various organic solvents such as alcohols and hydrocarbons has been traditionally preferred due to their superior performance. However, the principal limitations of these solvent type compositions include their inherent toxicity and flammability. While providing an ecological improvement over solvent based treatments, the existing organosiloxane emulsions and water dispersible silanes or siloxanes do not compare well with existing solvent-base silanes, silane/siloxanes combinations or siloxanes in terms of stability, penetration depth, and the beading effect of the treated substrate. Additionally, the use of surfactants may cause rewetting of the surface.

Therefore, there remains a need for a nonflammable aqueous composition useful for waterproofing inorganic substrates capable of providing at least equally efficient water resistance as solvent based compositions while also complying with VOC emission regulations. Accordingly, it is an object of the present invention to provide a nonflammable aqueous composition effectively suitable for imparting hydrophobicity to inorganic surfaces. More specifically, it is an object of this invention to provide the following three highly sought after characteristics for water repellants used on inorganic substrates: (1) a safer and environmentally acceptable aqueous solution, (2) imparting molecular level hydrophobicity and (3) reactivity with a substrate to provide long term performance.

BRIEF SUMMARY OF THE INVENTION

This invention is directed to ionic organosilicon compounds comprising ethylene glycol functionality and aqueous compositions comprising such ionic organosilicon compounds; wherein the compositions are suitable for applying to inorganic surfaces to impart water repellency to a wide variety of surfaces. The compositions of the present invention are prepared by dissolving ionic organosilicon compounds in water. Surprisingly, it has been found that the water soluble ionic organosilicon compounds, which have an ionic group, a hydrophobic group and at least one alkoxy group on silicon, of the present invention provide treated surfaces with excellent hydrophobicity. Until the present invention, these compounds have only been used in small quantities to solubilize silanes. The present invention satisfies the aforementioned needs by providing aqueous solutions comprising ionic organosilicon compounds dissolved in water.

Despite the water soluble nature of the ionic organosilicon compounds of the present invention, aqueous compositions of such compounds provide exceptional water resistance when applied to inorganic surfaces. All aqueous compositions of the present invention consist essentially of at least one ionic organosilicon compound comprising either ethylene glycol or polyethylene glycol functionality. Although desiring not to be held to the following explanation, it is believed that upon drying of the aqueous ionic organosilicon solution the molecular packing on the surface is such that the ionic group which enables solubility in water is buried deep within the structure after the silane forms chemical bonds with the inorganic surface. Accordingly, after application a treated surface may be characterized as having a long term water repellant layer. Thus, there are differences between what is taught in accordance with the concept of the present invention and what is disclosed in the prior art as evidenced by the several patents noted and discussed above.

DETAILED DESCRIPTION OF THE INVENTION

The present invention now will be described more fully hereinafter, in which some, but not all embodiments of the inventions are described. Indeed, these inventions may be embodied in many different forms and should not be construed as limited to the embodiments set forth herein; rather, these embodiments are provided so that this disclosure will satisfy applicable legal requirements.

Water soluble ionic organosilicon compounds including ethylene glycol or polyethylene glycol functionality of the present invention include compounds having a formula selected from the group consisting of;

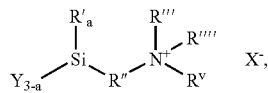

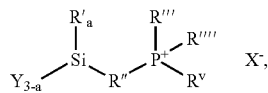 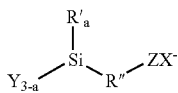

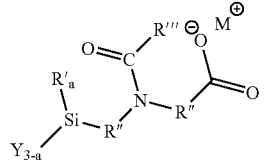 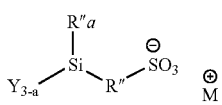

where in each formula:

Y is RO where R is $(CH_2CH_2O)_nH$ where n has a value of one through ten, $(CH_3OCH_2CH_2O)$, or $(CH_3CH_2OCH_2CH_2O)$ radical;

a has a value of zero, one and two;

R' is a methyl or ethyl radical;

R'' is an alkylene group one to four carbon atoms;

R''', R'''' and $R^v$ are alkyl groups containing one to twenty two carbon atoms wherein at least one such group is larger than eight carbon atoms, $—CH_2C_6H_5$, $—CH_2CH_2OH$, $—CH_2OH$, and $—(CH_2)_xNHC(O)R^{vi}$ wherein x has a value of from two to ten and $R^{vi}$ is a perfluoroalkyl radical having one to twelve carbon atoms;

X is chloride, bromide, fluoride, iodide, acetate or tosylate;

Z is a positively charged aromatic pyridinium ring of formula $C_5H_6N^+$; and

M is Na, K, or Li or H.

In one embodiment, the ionic organosilicon compounds of the formula:

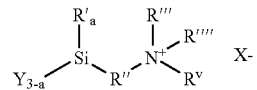

in which Y is RO where R is $(CH_2CH_2O)_nH$ where n has a value of one through ten, $(CH_3OCH_2CH_2O)$, or $(CH_3CH_2OCH_2CH_2O)$ radical; a has a value of zero; R'' is propylene; R''' is methyl or ethyl; R'''' and $R^v$ are alkyl groups containing one to twenty two wherein at least one such group is larger than eight carbon atoms and X is chloride, acetate or tosylate; may be dissolved in water to form an aqueous solution. Aqueous solutions comprising these ionic organosilicons may be applied to inorganic surfaces for imparting water resistance.

Specific examples of such ionic organosilicon compounds within the scope of the present invention are represented by the formulas:

(OH $CH_2CH_2O)_3Si(CH_2)_3N^+(CH_3)_2C_{18}H_{37}Cl^-$
(OH $CH_2CH_2O)_3Si(CH_2)_3N^+(CH_3)_2C_{18}H_{37}Br^-$
(OH $CH_2CH_2O)_3Si(CH_2)_3N^+CH_3(C_{10}H_{21})_2Cl^-$
(OH $CH_2CH_2O)_3Si(CH_2)_3N^+CH_3(C_{10}H_{21})_2Br^-$
(OH $CH_2CH_2O)_3Si(CH_2)_3N^+(CH_3)_2CH_2C_6H_5Cl^-$
(OH $CH_2CH_2O)_3Si(CH_2)_3N^+(CH_3)_2C_{18}H_{37}Cl^-$
(OH $CH_2CH_2O)_3Si(CH_2)_3N^+(CH_3)_2(CH_2)_3NHC(O)(CF_2)_6CF_3Cl^-$

In one embodiment, the ionic oganaoslicon compound may be selected from the formula;

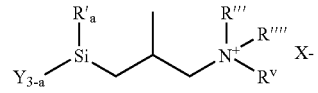

wherein:

Y is RO where R is an alkyl group with one to four carbons, $(CH_2CH_2O)_nH$ where n has a value of one through ten, $(CH_3OCH_2CH_2O)$, or $(CH_3CH_2OCH_2CH_2O)$ radical;

a has a value of zero, one and two;

R' is a methyl or ethyl radical;

R''', R'''' and $R^v$ are alkyl groups containing one to twenty two carbon atoms wherein at least one such group is larger than eight carbon atoms, $—CH_2C_6H_5$, $—CH_2CH_2OH$, $—CH_2OH$, and $—(CH_2)_xNHC(O)R^{vi}$ wherein x has a value of from two to ten and $R^{vi}$ is a perfluoroalkyl radical having one to twelve carbon atoms; and X is chloride, bromide, fluoride, iodide, acetate or tosylate.

Specific examples of such compounds include the following:

$(CH_3O)_3Si(CH_2CH(CH_3)CH_2N^+(CH_3)_2C_{18}H_{37}Cl^-$
$(CH_3O)_3Si(CH_2CH(CH_3)CH_2N^+(CH_3)_2C_{18}H_{37}Br^-$
$(CH_3O)_3Si(CH_2CH(CH_3)CH_2N^+CH_3(C_{10}H_{21})_2Cl^-$
$(CH_3O)_3Si(CH_2CH(CH_3)CH_2N^+CH_3(C_{10}H_{21})_2Br^-$
$(CH_3O)_3Si(CH_2CH(CH_3)CH_2N^+(CH_3)_2CH_2C_6H_5Cl^-$
$(CH_2CH_3O)_3Si(CH_2CH(CH_3)CH_2N^+(CH_3)_2C_{18}H_{37}Cl^-$
$(CH_3O)_3\ Si(CH_2CH(CH_3)CH_2N^{30}\ (CH_3)_2(CH_2)_3NHC(O)(CF_2)_6CF_3Cl^-$
$(OHCH_2CH_2O)_3Si(CH_2CH(CH_3)CH_2N^+(CH_3)_2C_{18}H_{37}Cl^-$
$(OHCH_2CH_2O)_3Si(CH_2CH(CH_3)CH_2N^+(CH_3)_2C_{18}H_{37}Br^-$ $(OHCH_2CH_2O)_3Si(CH_2CH(CH_3)CH_2N^+CH_3(C_{10}H_{21})_2$
  $Cl^-$
$(OHCH_2CH_2O)_3Si(CH_2CH(CH_3)CH_2N^+CH_3(C_{10}H_{21})_2$
  $Br^-$
$(OHCH_2CH_2O)_3Si(CH_2CH(CH_3)CH_2N^+(CH_3)_2$
  $CH_2C_6H_5Cl^-$
$(OHCH_2CH_2O)_3Si(CH_2CH(CH_3)CH_2N^{30}$ $(CH_3)_2(CH_2)_3$
  $NHC(O)(CF_2)_6CF_3Cl^-$

In another alternative embodiment, the ionic organosilicon compound may be selected from the formula:

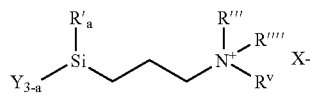

wherein;

Y is RO where R is $(CH_2CH_2O)_nH$ where n has a value of one through ten, $(CH_3OCH_2CH_2O)$, or $(CH_3CH_2OCH_2CH_2O)$ radical;

a has a value of zero, one and two;

R' is a methyl or ethyl radical;

R''', R'''' and R$^v$ are alkyl groups containing one to twenty two carbon atoms wherein at least one such group is larger than eight carbon atoms, $-CH_2C_6H_5$, $-CH_2CH_2OH$, $-CH_2OH$, and $-(CH_2)_xNHC(O)R^{vi}$ wherein x has a value of from two to ten and R$^{vi}$ is a perfluoroalkyl radical having one to twelve carbon atoms; and X is chloride, bromide, fluoride, iodide, acetate or tosylate.

Specific examples of such compounds include the following:

$(OHCH_2CH_2O)_3Si(CH_2)_3N^+(CH_3)_2C_{18}H_{37}Cl^-$
$(OHCH_2CH_2O)_3Si(CH_2)_3N^+(CH_3)_2C_{18}H_{37}Br^-$
$(OHCH_2CH_2O)_3Si(CH_2)_3N^+CH_3(C_{10}H_{21})_2Cl^-$
$(OHCH_2CH_2O)_3Si(CH_2)_3N^+CH_3(C_{10}H_{21})_2Br^-$
$(OHCH_2CH_2O)_3Si(CH_2)_3N^+(CH_3)_2CH_2C_6H_5Cl^-$
$(OHCH_2CH_2O)_3Si(CH_2)_3N^+(CH_3)_2(CH_2)_3NHC(O)$
  $(CF_2)_6CF_3Cl^-$

It has been found that by including ethylene glycol or polyethylene glycol functionality as indicated in the formulas provided above, many beneficial results are realized. Specifically, compositions containing ethylene glycol or polyethylene glycol functionality are (1) more soluble in water; (2) less flammable; (3) increased water solution stability from 12 hours provided by methoxy and ethoxy groups to over 72 hours; (4) and reduced toxicity due to elimination of volatile methanol and ethanol constituents.

In another alternative embodiment, the ionic organosilicon compounds corresponding to the formulas 3-(trimethoxysilyl)propyldimethyloctadecyl ammonium chloride, 3-(trimethoxysilyl)propylmethyldidecyl ammonium chloride, and 3-(trimethoxysilyl)propyldimethylhexadecyl ammonium chloride are especially suitable for aqueous solutions for application to inorganic surfaces in accordance with the present invention. Structures for these ionic organosilicon compounds are as follows:

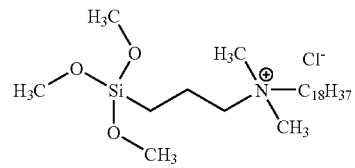

3-(trimethoxysilyl)propyldimethyloctadecyl ammonium chloride;

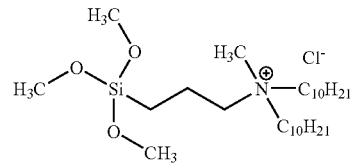

3-(trimethoxysilyl)propylmethyldidecyl ammonium chloride; and

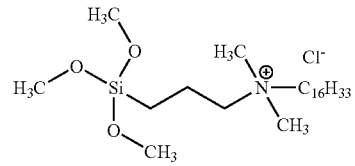

3-(trimethoxysilyl)propyldimethylhexadecyl ammonium chloride.

The compositions in accordance with the present invention are made by dissolving an ionic organosilicon in water. Additionally, more than one ionic organosilicon compound can be dissolved in water to formulate an aqueous solution comprising more than one ionic organosilicon compound. Furthermore, some compositions in accordance with the present invention may also include known excipients such as for example wetting agents, surfactants, and antimicrobial agents. These solutions comply with the local state and federal regulations regarding volatile organic content (VOC) with desired application dosage and can be applied to a wide variety of surfaces by any known means including for example by brush, roller, air spray, and airless spray techniques. After an aqueous solution comprising an ionic organosilicon is applied and allowed to dry, a treated surface is obtained comprising a protective water resistant layer bonded to the substrate. Although wishing not to be held to the following explanation, it is believed that upon drying the molecular packing on the surface is such that the ionic group which enables solubility in water is buried deep within the structure after the silane forms chemical bonds with the surface. Furthermore, it is believed that the long chain on the central ionic group prohibits water from reaching the soluble ionic part of the molecule. Accordingly, the present invention also provides treated surfaces comprising a unique layer in which the soluble components are shielded from water by long chains attached to the soluble component.

Any surface with functional groups that will bond with the silanols created by hydrolysis of the silane alkoxy groups may be rendered water repellant upon treatment with aqueous solutions of the present invention. Some suitable surfaces for example include heavy and light weight concrete, masonry products, gypsum, concrete blocks, cinder blocks, soft mud bricks, sand lime bricks, drain tiles, ceramic tiles, sandstone, plaster, clay bricks, natural stones and rocks, roofing tiles, calcium silicate bricks, cement articles, slag stones and bricks, stucco, limestone, macadam, marble, grouts, mortar, terrazzo, clinker, pumice, terra, cotta, porcelain, adobe, coral, dolomite and asphalt. Non-cement surfaces may be treated with compositions of the present invention including but not limited to perlite, cellular glass, vermiculite, mica, silica and diatomaceous earth.

In one embodiment, the ionic organosilicon composition may include at least about 0.1 weight percent of an ionic organosilicon compound. Additionally, some embodiments may include between about 0.1 and about 10 weight percent of an ionic orgaosilicaon compound while others may comprise between about 10 and 99 weight percent or preferably about 20 and 60 weight percent of an organosilicon compound.

EXAMPLE 1

3-[tri-(2-hydroxyethoxy)silyl]propyldimethyloctadecyl ammonium chloride

A two liter, three-necked flask equipped with a condenser, stirrer, thermometer and a distillation head, was charged with 360 grams (six moles) of ethylene glycol. To this solution, 200 grams of -3-chloropropyltrimethoxysilane was added drop-wise at 100° C. over a period of two hours. The mixture was heated for six hours at 100° C. during which time 101 grams of material, chiefly methanol boiling below 100° C., was recovered. 460 grams of a crude product mixture was obtained.

The structure of the major component of the crude product mixture was $(OHCH_2CH_2O)_3SiCH_2CH(CH_3)CH_2Cl$:

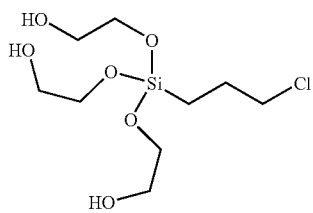

3-chloropropyl-tri-(2-hydroxy-ethoxy) silane

In the same reaction configuration, 265 grams (0.9 mole) of octadecyldimethylamine was added to the crude product solution. This mixture was heated to 120° C. for 20 hours. After 20 hours the reaction was complete. Titration of a sample of the product mixture showed the chloride ion concentration to be 4.35%. The structure of the major component was $(OHCH_2CH_2O)_3SiCH_2CH_2CH_2N(CH_3)_2C_{18}H_{37}Cl-$:

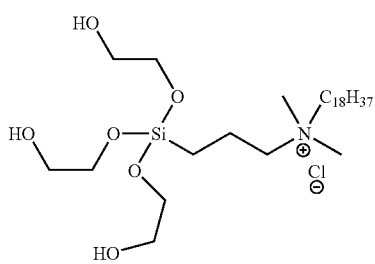

3-[tri-(2-hydroxyethoxy)silyl]propyldimethyloctadecyl ammonium chloride

The calculated chloride ion concentration for the product mixture was 4.40%. The product was miscible with water in all proportions.

EXAMPLE 2

A two liter, three-necked flask equipped with a condenser, stirrer, thermometer and a distillation head, was charged with 636 grams (six moles) of diethylene glycol. To this solution, 200 grams of -3-chloropropyltrimethoxysilane was added drop-wise at 100° C. over a period of two hours. The mixture was heated for six hours at 125° C. during which time 101 grams of material, chiefly methanol boiling below 100° C., was recovered. 735 grams of a crude product mixture was obtained.

The major component of the crude product mixture was $(OHCH_2CH_2OCH_2CH_2O)_3SiCH_2CH(CH_3)CH_2Cl$:

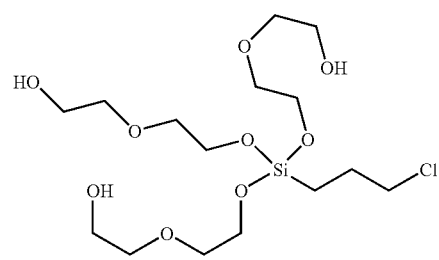

In the same reaction configuration, 265 grams (0.9 mole) of octadecyldimethylamine was added to the crude product solution. This mixture was heated to 120° C. for 20 hours. After 20 hours the reaction was complete. Titration of a sample of the product mixture showed the chloride ion concentration to be 2.97%. The structure of the major component was $(OHCH_2CH_2OCH_2CH_2O)_3SiCH_{H2}CH_2CH_2N(CH_3)_2 C_{18}H_{37}Cl-$:

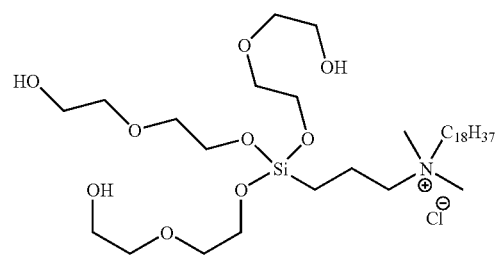

The calculated chloride ion concentration for the product mixture was 3.2%. The product was miscible with water in all proportions

EXAMPLE 3

3-(trimethoxysilyl)-2-methylpropyldimethyloctadecyl ammonium chloride

A two liter, pressure reactor equipped with a stirrer, thermometer, was charged with 225 grams of -3-chloro-2-methylpropyl-trimethoxysilane (1.1 mole), 295 grams of dimethyloctadecylamine (1.0 mole) and 100 grams of methanol. The mixture was heated for 30 hours at 120° C. After 30 hours the reaction was complete. Titration of a sample of the product mixture showed the chloride ion concentration to be 5.62%.

The structure of the major component was $(CH_3O)_3SiCH_2CH(CH_3)CH_2N(CH_3)_2C_{18}H_{37}Cl^-$:

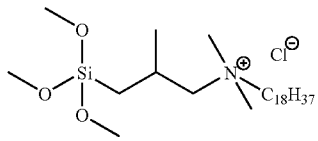

3-(trimethoxysilyl)-2-methylpropyldimethyloctadecyl ammonium chloride

The calculated chloride ion concentration for the product mixture was 5.71%. The product was miscible with water in all proportions.

EXAMPLE 4

3-[tri-(2-hydroxyethoxy)silyl]-2-methylpropyldimethyloctadecyl ammonium chloride A Two liter, three-necked flask equipped with a condenser, stirrer, thermometer and a distillation head, was charged with 360 grams (six moles) of ethylene glycol. 212 grams of -3-chloro-2-methylpropyl-trimethoxysilane was added drop-wise to the solution at 100° C. over a period of two hours. The mixture was heated for six hours at 100° C. during which time 101 grams of material, chiefly methanol boiling below 100° C., was recovered. 470 grams of crude product mixture was obtained. The structure of the major trans-esterified product was $(OHCH_2CH_2O)_3SiCH_2CH(CH_3)CH_2Cl$;

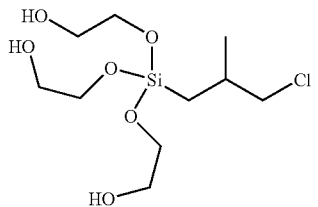

3-chloro-2-methylpropyl-tri-(2-hydroxy-ethoxy) silane

In the same reaction configuration, 265 grams (0.9 mole) of octadecyldimethylamine was added to the crude product solution. The mixture was heated to 120° C. for 20 hours. After 20 hours the reaction was complete. Titration of a sample of the product mixture showed the chloride ion concentration to be 4.17%. The structure of the major component was $(OHCH_2CH_2O)_3SiCH_2CH(CH_3)CH_2N(CH_3)_2C_{18}H_{37}Cl^-$:

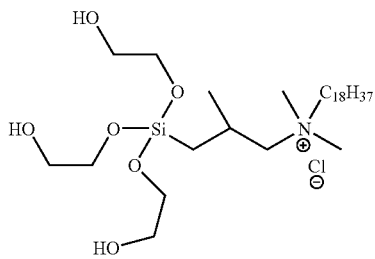

3-[tri-(2-hydroxyethoxy)silyl]-2-methylpropyldimethyloctadecyl ammonium chloride The calculated chloride ion concentration for the product mixture was 4.32%. The product was miscible with water in all proportions.

EXAMPLE 5

A two liter, three-necked flask equipped with a condenser, stirrer, thermometer and a distillation head, was charged with 540 grams (six moles) of ethyleneglycolmonoethyl ether. To this solution, 200 grams of -3-chloropropyltrimethoxysilane was added drop-wise at 100° C. over a period of two hours. The mixture was heated for six hours at 125° C. during which time 101 grams of material, chiefly methanol boiling below 100° C., was recovered. 735 grams of a crude product mixture was obtained.

The major component of the crude product mixture was $(CH_3CH_2OCH_2CH_2O)_3SiCH_2CH(CH_3)CH_2Cl$:

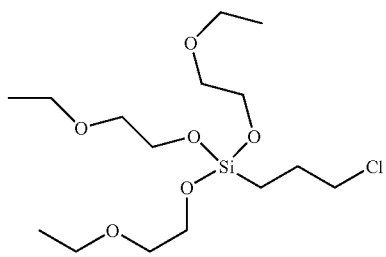

3-Chloropropyltri(2-ethoxyethoxy)silane

In the same reaction configuration, 265 grams (0.9 mole) of octadecyldimethylamine was added to the crude product solution. This mixture was heated to 120° C. for 20 hours. After 20 hours the reaction was complete. Titration of a sample of the product mixture showed the chloride ion concentration to be 3.45%. The structure of the major component was $(CH_2CH_3OCH_2CH_2O)_3SiCH_2CH_2CH_2N(CH_3)_2C_{18}H_{37}Cl^-$:

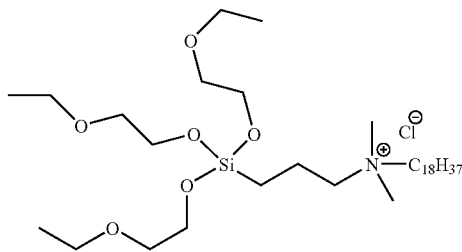

3-[tri-(2ethoxyethoxy)silyl]propyldimethyloctadecyl ammonium chloride

The calculated chloride ion concentration for the product mixture was 3.52%. The product was miscible with water in all proportions.

EXAMPLE 6

Multiple aqueous solutions ranging from 0.1 to 5.0 weight percent of 3-(trimethoxysilyl)propyldimethyloctaldecyl ammonium chloride were prepared by dissolution in tap water. The substrates treated included a piece of a concrete block, a cement sheet, a sand face plaster, and sandstone. These materials were weighed and dried in an oven at 100° C. until a constant weight was reached. The pieces were then weighed and placed in 1-cm of water for 1 hour, weighed again, and dried in a 100° C. oven until a constant weight was reached. At which time, the individual pieces were weighed, soaked in the water repellent solution for 20 seconds, then dried, and finally reweighed. The treated samples were placed in 1 cm of water for 1 hour and weighed. The percent water exclusion for each experiment is provided in Table-I; wherein the percent water exclusion was calculated in the following manner:

$$\frac{(\text{water pickup of untreated substrate} - \text{water pickup of treated substrate}) \times 100}{\text{Water pickup of untreated substrate.}}$$

TABLE-I (%) Water exclusion with different concentrations

| | Water Exclusion (%) | | | | | | | |
|---|---|---|---|---|---|---|---|---|
| Concentration | 0.1 | 0.5 | 1.0 | 1.5 | 2.0 | 2.5 | 3.5 | 5.0 |
| Concrete Block | 60 | 68 | 72 | 82 | 87 | 89 | 85 | 82 |
| Cement Sheet | 59 | 67 | 73 | 88 | 87 | 89 | 88 | 83 |
| Sand face Plaster | 70 | 73 | 75 | 82 | 86 | 90 | 89 | 83 |
| Sand Stone | 69 | 76 | 78 | 93 | 93 | 92 | 91 | 91 |

These results reveal that 1.5-3.5 weight percent solutions provide excellent hydrophobicity for most substrates.

EXAMPLE 7

Standard M20 block samples were used for testing. The standard size bricks was cut into three equal parts for testing. The sandstone pieces were 7-cm×6-mm×7-cm. An untreated control was included for comparison and to calculate water exclusion. The samples were cleaned with a wire brush and cloth. The pieces were weighed and dried in an oven at 100° C. until a constant weight was reached. The water uptake was determined by the procedures established according to ASTM D-6489. The pieces were weighed and placed in 1-cm of water for 24 hours, weighed again and dried in a 100° C. oven until a constant weight was reached. The pieces were then treated with a water repellent as described in example 5. After soaking in 1 cm of water for 24 hours, the pieces were weighed again. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

A 2.5 weight percent solution of 3-(trimethoxysilyl)propyldimethyloctadecyl ammonium chloride was prepared by dissolving in tap water. Three samples of each substrate were treated by dipping the sample for 20 seconds. The samples were allowed to cure for 24 hours. They were further dried in an oven at 100° C. for one hour. After removal from the oven, the samples were allowed to attain room temperature before measurements were taken. Water uptake was determined using ASTM method D6489. The calculated results of the average of three samples are summarized in Table-II

TABLE II

Water exclusion based on ASTM D6489

| Substrate | % Water Exclusion |
|---|---|
| Concrete Block (M20) | 89 |
| Brick | 90 |
| Sandstone | 85 |
| Cement Sheet | 80 |

EXAMPLE 8

Rilem Hydraulic Water Penetration Test (Test II.4)

A 2.5% solution of 3-(trimethoxysilyl)propyldimethyloctadecyl ammonium chloride was prepared by dissolving in tap water. Three samples of each substrate were treated by dipping the sample in the aqueous solution for 20 seconds. The samples were allowed to cure for 24 hours. Then they were further dried in an oven at 100° C. for one hour. The samples were allowed to attain room temperature before measurements were taken. An uptake tube was affixed to substrate's surface by interposing a strip of caulk between the circular brim of the tube and the surface of the masonry material with applied pressure. Water was then added to the opening in the tube until it reached the zero graduation mark. The quantity of water absorbed by the substrate in 20 minutes is read from the graduation marks on the tube. The data is provided in Table-III which shows milliliters (mls) lost in 20 minutes.

TABLE III

Rilem hydraulic water penetration test (Test II.4)

| Substrate | Untreated Water Loss in 20 minutes ml | 2.5% Treated Water Loss in 20 minutes Ml |
|---|---|---|
| Concrete Block (M20) | 8.0 | 0.2 |
| Brick | 40 | 0.2 |
| Sandstone | 20 | 0.1 |
| Cement Sheet | 10 | 0.3 |

EXAMPLE 9

Depth of Penetration

A 2.5% solution of 3-(trimethoxysilyl)propyldimethyloctadecyl ammonium chloride was prepared by dissolving in tap water. Three samples of each substrate were treated by dipping the sample in the aqueous solution for 20 seconds. The samples ware allowed to cure for 24 hours. Then they were further dried in an oven at 100° C. for one hour. The samples were allowed to attain room temperature before measurements were taken. Each sample was split longitudinally using a hammer and chisel. One half of each sample was placed fractured surface down in a water soluble dye solution. Only the untreated portion of each sample absorbed the solution and became stained. The depth of penetration was measured from the surface down to the stained region. The average penetration is provided in Table-IV.

TABLE IV

| | Depth of Penetration | | |
|---|---|---|---|
| Substrate | 2.5% Treatment Depth of Penetration mm | Treatment Time (Seconds) | Amount of Solution Absorption (%) |
| Concrete Block (M20) | 6 | 20 | 1 |
| Brick | 10 | 20 | 2 |
| Sandstone | 3 | 20 | 0.3 |

EXAMPLE 10

Capillary Absorption Test

After conditioning, samples of treated and untreated concrete cubes were taken for further experimentation. Initial weights of all the cubes were recorded. The weighed samples were placed in a container on a porous support made from a pack of filter papers. The thickness of the pack was approximately 1 cm. The pack of filter papers ensures immediate and continuous contact between water and only the surface on which the samples were resting. Tap water was slowly poured into the container until the paper was completely saturated. The water level was not allowed to rise beyond the top border of the pack. For reducing evaporation of water, the container was covered with a glass sheet.

For assessing the capillary water absorption, the samples were removed from the container after one hour. After wiping the surface in contact with water with a damp cloth, each sample was weighed. The results obtained are provided in Table-V.

TABLE V

| | Capillary Absorption | |
|---|---|---|
| Substrate | Untreated Amount water absorbed (%) | 2.5% Treatment Amount of water absorbed (%) |
| Concrete Block (M20) | 5 | <0.1 |
| Brick | 10 | <0.1 |

EXAMPLE 11

Standard M20 block samples were used for additional testing. An untreated control was included for comparison and to calculate water exclusion. The samples were cleaned with a wire brush and cloth. The pieces were weighed and dried in an oven at 100° C. until a constant weight was reached. The water uptake was determined by the procedures established according to the ASTM D-6489. The pieces were weighed and placed in 1-cm of water for 24 hours, weighed again and dried in a 100° C. oven until a constant weight was reached. A 2.5 weight % solution of 3-(trimethoxysilyl)propylmethyldidecyl ammonium chloride was prepared by dissolving in tap water. These samples were treated by dipping in the aqueous solution for 20 seconds. The samples were allowed to cure for 24 hours. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 87%.

EXAMPLE 12

Standard M20 block samples were used for testing. An untreated control was included for comparison and to calculate water exclusion. The samples were cleaned with a wire brush and cloth. The pieces were weighed and dried in an oven at 100° C. until a constant weight was reached. A 2.5 weight % solution of 3-(trimethoxysilyl)propyldimethylhexadecyl ammonium chloride was prepared by dissolving in tap water. Three samples were treated by dipping in the aqueous solution for 20 seconds. The samples were allowed to cure for 24 hours. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 85%.

EXAMPLE 13

Standard M20 block samples were used for testing. An untreated control was included for comparison and to calculate water exclusion. The samples were cleaned with a wire brush and cloth. The pieces were weighed and dried in an oven at 100° C. until a constant weight was reached. A 2.5 weight % solution was prepared by dissolving the product obtained from example 1, in tap water. Three samples were treated by dipping in the aqueous solution for 20 seconds. The samples were allowed to cure for 48 hours. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 91%.

EXAMPLE 14

Standard M20 block samples were used for testing. An untreated control was included for comparison and to calculate water exclusion. The samples were cleaned with a wire brush and cloth. The pieces were weighed and dried in an oven at 100° C. until a constant weight was reached. A 2.5 weight % solution was prepared by dissolving the product obtained from example 2, in tap water. Three samples were treated by dipping in the aqueous solution for 20 seconds. The samples were allowed to cure for 5 days. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 81%.

EXAMPLE 15

Standard M20 block samples were used for testing. An untreated control was included for comparison and to calculate water exclusion. The samples were cleaned with a wire brush and cloth. The pieces were weighed and dried in an oven at 100° C. until a constant weight was reached. A 2.5 weight % solution was prepared by dissolving the product obtained from example 4, in tap water. Three samples were treated by dipping in the aqueous solution for 20 seconds. The samples were allowed to cure for 48 hours. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 93%.

EXAMPLE 16

Standard M20 block samples were used for testing. An untreated control was included for comparison and to calculate water exclusion. The samples were cleaned with a wire brush and cloth. The pieces were weighed and dried in an oven at 100° C. until a constant weight was reached. A 2.5 weight % solution was prepared by dissolving the product obtained from example 5, in tap water. Three samples were treated by dipping in the aqueous solution for 20 seconds. The samples were allowed to cure for 48 hours. Then they were further dried in an oven at 100° C. for one hour. The samples were allowed to attain room temperature before measurements were taken. Water uptake, percent water absorption (water uptake×100/Weight of dry piece) and % water exclusion were calculated by:

$$\frac{(\text{water uptake of control} - \text{water uptake of treated sample}) \times 100}{\text{water uptake of control}}$$

The average water exclusion calculated for three samples was 93%.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An ionic organosilicon compound selected from the formula:

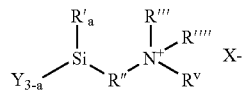

where in each formula:
Y is RO where R is $(CH_2CH_2O)_nH$ where n has a value of one through ten;
a has a value of zero, one and two;
R' is a methyl or ethyl radical;
R" is an alkylene group with four carbon atoms;
R''', R'''' and $R^v$ are alkyl groups containing one to twenty two carbon atoms wherein at least one such group is larger than eight carbon atoms, —$CH_2C_6H_5$, —$CH_2CH_2OH$, —$CH_2OH$, and —$(CH_2)_xNHC(O)R^{vi}$ wherein x has a value of from two to ten and $R^{vi}$ is a perfluoroalkyl radical having one to twelve carbon atoms; and
X is chloride, bromide, fluoride, iodide, acetate or tosylate.

2. An ionic organosilicon compound according to claim 1, wherein said compound is selected from the formula:

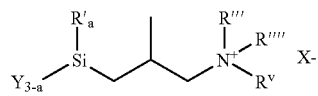

wherein:
Y is RO where R is an alkyl group with one to four carbons, $(CH_2CH_2O)_nH$ where n has a value of one through ten;
a has a value of zero, one and two;
R' is a methyl or ethyl radical;
R''', R'''' and $R^v$ are alkyl groups containing one to twenty two carbon atoms wherein at least one such group is larger than eight carbon atoms, —$CH_2C_6H_5$, —$CH_2CH_2OH$, —$CH_2OH$, and —$(CH_2)_xNHC(O)R^{vi}$ wherein x has a value of from two to ten and $R^{vi}$ is a perfluoroalkyl radical having one to twelve carbon atoms; and
X is chloride, bromide, fluoride, iodide, acetate or tosylate.

3. An ionic organosilicon compound according to claim 1, wherein said compound is 3-[tri-(2-hydroxyethoxy)silyl]-2-methylpropyldimethyloctadecyl ammonium chloride.

4. An aqueous composition consisting essentially of at least one water soluble ionic organosilicon compounds of claim 1.

5. The aqueous composition of claim 4; wherein said composition consists essentially of only one ionic organosilicon compound.

6. The aqueous composition of claim 4; wherein said water soluble ionic organosilicon compound consists essentially of between 0.1 to 10 weight percent of said aqueous composition.

7. The aqueous composition of claim 4; wherein said water soluble ionic organosilicon compound is 3-[tri-(2-hydroxyethoxy)silyl]-2- methylpropyldimethyloctadecyl ammonium chloride.

8. An aqueous composition comprising at least one water soluble ionic organosilicon compound of claim 1.

9. The aqueous composition of claim 8; wherein said composition comprises of only one ionic organosilicon compound.

10. The aqueous composition of claim 8; wherein said water soluble ionic organosilicon compound comprises between about 0.1 to 10 weight percent of said aqueous composition.

11. The aqueous composition of claim 8; wherein said water soluble ionic organosilicon compound is 3-[tri-(2-hydroxyethoxy)silyl]-2-methylpropyldimethyloctadecyl ammonium chloride.

* * * * *